United States Patent [19]

Kuriyama et al.

[11] Patent Number: 5,783,550
[45] Date of Patent: Jul. 21, 1998

[54] MOLD REMOVAL COMPOSITION AND MOLD BLEACHING METHOD

[75] Inventors: Yasuhisa Kuriyama; Jun Kokubu, both of Yokkaichi; Yasuo Hiro, Suzuka; Yoshiko Tsuji, Yokkaichi; Tsuneo Kobayashi, Ninomiya-Machi; Masahito Mikami, Hadano; Shuzo Nakamura, Minoo, all of Japan

[73] Assignee: S. C. Johnson & Son, Inc., Racine, Wis.

[21] Appl. No.: 793,532

[22] PCT Filed: Aug. 30, 1995

[86] PCT No.: PCT/JP95/01717

§ 371 Date: Jul. 2, 1997

§ 102(e) Date: Jul. 2, 1997

[87] PCT Pub. No.: WO96/06911

PCT Pub. Date: Mar. 7, 1996

[30] Foreign Application Priority Data

Aug. 31, 1994 [JP] Japan ................ 6-229044

[51] Int. Cl.$^6$ ................ C11D 3/39; A01N 59/24
[52] U.S. Cl. ................ 510/372; 8/111; 510/313; 510/314; 510/303; 510/191; 510/238; 510/239; 252/186.38; 252/186.41; 252/186.42; 422/28; 422/35

[58] Field of Search ................ 8/111; 510/313, 510/314, 303, 372, 191, 238, 239; 252/186.38, 186.41, 186.42; 422/28, 35

[56] References Cited

U.S. PATENT DOCUMENTS

| 3,163,606 | 12/1964 | Viveen et al. | 510/313 |
| 3,756,774 | 9/1973 | Kirner | 8/111 |
| 4,025,453 | 5/1977 | Kravetz et al. | 510/314 |
| 4,086,175 | 4/1978 | Kravetz et al. | |
| 4,086,177 | 4/1978 | Kubitschek et al. | |
| 4,199,466 | 4/1980 | Benson, Jr. | |

FOREIGN PATENT DOCUMENTS

8475  3/1980  European Pat. Off. .

*Primary Examiner*—Alan Diamond

[57] ABSTRACT

A mold removal composition useful to remove molds adhered to furnishing and walls of homes, particularly kitchen sinks and bathroom walls, ceilings, and tiles, and a mold bleaching method are provided. The mold removal composition contains peroxide, dicyandiamide, alkali metal hydroxide or alkaline-earth metal hydroxide, and water. Its pH is 8.0–13.0.

2 Claims, No Drawings

MOLD REMOVAL COMPOSITION AND MOLD BLEACHING METHOD

This application is a 371 of PCT/JP95/01717 filed Aug. 30, 1995.

TECHNICAL FIELD

The present invention relates to a peroxide mold removal composition which has superior strength with respect to removing mold and does not have an irritating odor.

BACKGROUND OF THE INVENTION

In order to bleach the mold adhered to the walls and furniture in homes, chlorine bleaching in which sodium hypochlorite is used as the main component has been conventionally used. However, although chlorine bleaching agents have a superior bleaching strength, there are disadvantages including providing discomfort to the user due to the peculiar odor generated by the molecular chlorine as well as concerns regarding the toxic effects of chlorine gas, depending on the method of use. Furthermore, there is the concern that chlorine bleaching agents form environmentally undeniable organic chlorine compounds as by-products. Accordingly, switching to a bleaching agent that does not use a chlorine compound is desired.

In order to remove soil adhered to the walls and furnishings in a home, particularly the kitchen sink and bathroom walls, ceiling and tiles, a strong removing or bleaching function with respect to mold is necessary. However, molds manifest strong resistance with respect to conventional bleaching agents; thus, completely bleaching the mold is very difficult compared to bleaching fabrics, etc. Namely, peroxide bleaching agents such as hydrogen peroxide, inorganic peroxides, organic peroxides, etc., used independently have weak bleaching strength with respect to molds, and it is difficult to bleach the molds completely with them.

With regard to improvements in the bleaching action of peroxide bleaching agents, various proposals have been made. In Japanese Kokai Patent Application No. Sho 61[1986]-42600 in particular, the combination of glucose pentaacetate, tetraacetylethylenediamine, tetraacetylglycoluril, cyanamide, etc., as activating agent with an oxygen bleaching agent is disclosed. However, the disclosed compositions containing an activating agent have problems with the bleaching strength, with respect to molds not being strong enough, compounds with irritating odors being created as by-products by the reaction with hydrogen peroxide and not being suited for practical application.

Also, in Japanese Kokai Patent Application No. Sho 52[1977]-110287, a composition for fabric bleaching agent composed of a peroxide and cyanamide and/or a metal cyanamide is disclosed, but the bleaching strength is not strong enough with respect to molds. In U.S. Pat. No. 3,756,774, a composition for a fabric bleaching agent with a pH of 4–7 containing organic cyanides and peroxides is disclosed, but the bleaching strength with respect to molds is not sufficient. In Japanese Kokai Patent Application No. Sho 62[1987]-1790, a mold removal composition containing peroxide and silicone oil and/or emulsifier is disclosed, but the bleaching strength with respect to molds is not sufficient.

SUMMARY DISCLOSURE OF INVENTION

The objective of said invention is to provide a mold removal composition having superior bleaching strength with respect to molds adhered to walls and furnishing in homes, particularly, kitchen sinks and bathroom walls, ceiling and tiles, and a bleaching method for said molds. As a result of earnest research, said inventors found that a composition of a peroxide and dicyandiamide manifests extremely high bleaching strength with respect to molds and does not have an irritating odor.

BEST MODE FOR CARRYING OUT THE INVENTION

As the peroxide used as component (A) of said invention, commercially available hydrogen peroxide aqueous solutions can be used favorably. The blending amount of the hydrogen peroxide aqueous solution in the mold removal composition of the present invention is generally 0.5–60 wt %, preferably 0.5–30 wt %, and more preferably 0.5–10 wt %. For practicality, 1–6 wt % is most favorable.

Also, it is possible to use as the peroxide a compound that forms an adduct with hydrogen peroxide and forms hydrogen peroxide insitu in an aqueous solution. As the compound that forms an adduct with hydrogen peroxide, sodium percarbonate, which is obtained by adding sodium carbonate and hydrogen peroxide in a 2:3 molar ratio, sodium perborate monohydrate and sodium perborate tetrahydrate, in which sodium borate and hydrogen peroxide are added in a 1:1 molar ratio, etc., can be cited. When a compound comprising an adduct with hydrogen peroxide is used, a quantity is used such that the quality of hydrogen peroxide produced by dissociation of the adduct in an aqueous solution is in the desired range.

Next, as the dicyandiamide used as component (B), a commercially available solid or aqueous solution can be used.

The content of the peroxide used as component (A) in the mold removal composition is generally 0.5–60 wt %, preferably 0.5–30 wt %, and more preferably 0.5–10 wt %. For practicality, 1–6 wt % is most favorable. The content of dicyandiamide which is component (B) is 0.2–30 wt %, preferably 0.5–10 wt %, and more preferably 0.5–5 wt %. If component (A) or (B) is lower than said range, the bleaching action is low, when component (A) or (B) is greater than said range, [the product] becomes difficult to handle as a mold removal composition.

The pH of the mold removal composition in said invention is important for obtaining high bleaching strength; normally it is 8.0–13.0, preferably 9.0–12.0, and more preferably 9.0–11.5. If the pH is lower than said range, the bleaching activity is low. If the pH is higher than said range, handling [the product] as a mold removal composition becomes difficult; as the peroxide may become unstable.

In said invention, an alkali metal hydroxide or alkaline-earth metal hydroxide (C) is used for adjusting the pH of the mold removal composition to said range. The alkali metal hydroxide or alkaline-earth metal hydroxide (C) is used in quantity such that the pH of the mold removal composition is contained within said range. Also, when sodium percarbonate or sodium perborate, etc., is used as the agent for generating hydrogen peroxide, the aqueous solution of said adduct is itself alkaline, so it is possible to reduce the quantity of alkali metal hydroxide or alkaline-earth metal hydroxide (C) used.

As example of alkali metal hydroxide or alkaline-earth metal hydroxide (C), alkali metal hydroxides such as lithium hydroxide, sodium hydroxide, potassium hydroxide, etc., and alkaline-earth metal hydroxides such as magnesium hydroxide, calcium hydroxide, barium hydroxide, etc., can be mentioned. Among these, sodium hydroxide and calcium hydroxide are favorable.

The content of alkali metal hydroxide or alkaline-earth hydroxide used as component (C) is selected from a range of 0.1–10 wt %; it need only be used in the quantity required to obtain a pH of the solution of the mold removal composition of 8.0–13.0.

The mold removal composition of the present invention is normally manufactured by dissolving hydrogen peroxide or the compound forming an adduct with hydrogen peroxide (A) and dicyandiamide (B) in water. The mold removal composition of the present invention can be a uniform aqueous solution or an aqueous slurry. The content of water (D) used as the solvent of the mold removal composition in said invention is selected from a range of 40–99 wt %, preferably 50–98 wt %, and more preferably 60–97 wt %.

In the mold removal composition of the present invention, it is preferable to add a surfactant. As the surfactant, nonionic surfactant such as polyoxyethylene alkyl ethers, polyoxyethylene fatty acid esters, amine oxides, etc., and anionic surfactants such as soaps, alkyl sulfates, and alkylbenzenesulfonates, etc., can be utilized. It is preferable for the quantity of the surfactant added to be 0.1–5 wt % in the mold removal composition. By the addition of a surfactant, it is possible to assist in the penetration of the mold removal composition with respect to the mold and to enhance the mold bleaching and washing/removing effect.

The mold removal composition of the present invention is used as a slurry or a solution, and it is possible to bleach the mold effectively by coating with a brush or sponge, etc., or spraying with a sprayer, etc., on the surfaces of the furnishing or walls of a home which are coated with molds.

The following examples are provided to show various aspects of the invention without departing from the spirit and scope of the invention. Unless otherwise indicated, all parts and percentages used in the Examples and Comparative Examples are by weight.

APPLICATION EXAMPLE 1

A mold removal composition was prepared by mixing and dissolving hydrogen peroxide aqueous solution, dicyandiamide, and sodium hydroxide in water to obtain a hydrogen peroxide concentrate of 3.0 wt %, a dicyandiamide concentration of 3.0 wt %, and a sodium hydroxide concentration of 2.0 wt %. The pH of the mold removal composition was 11.4.

Next, a mold bleaching test and an odor evaluation were carried out as follows by using the obtained mold remover composition. The results are shown in Table I.

Testing method and evaluation method for mold bleaching test

1) Mold culture method

An agar culture medium which was steam sterilized is transferred into a sterilized petri dish. Black mold (*Aureobasidium pullulans*) is transplanted into the agar culture medium and cultured by being placed in a 28° C. incubator for 20 days.

2) Mold bleaching test method

A glass tube is inserted into the agar grown with black mold, the prepared mold removal composition is placed inside the glass tube, and the extend of black mold bleaching after standing for 30 minutes is observed.

3) Evaluation method

The extent of bleaching is judged visually according to the following 3 levels:

a) Bleached degree III: Totally bleached.

b) Bleached degree II: Bleached to some extent.

c) Bleached degree I: Hardly or totally not bleached.

Odor testing and evaluation method

1) Odor testing method 10 panelists smell the odor of the mold removal composition to carry out functional evaluation.

2) Odor evaluation method

The odor is evaluated as follows:

o: Most or all panelists do not sense an irritating or bad odor.

Δ: About half of the panelists sense an irritating or bad odor.

x: Most or all panelists sense an irritating or bad odor.

APPLICATION EXAMPLES 2–4

Mold removal compositions were prepared by varying the quantity of each component as indicated in Table I. % indicates weight percent. The pH of the mold removal composition was as indicated in Table I.

Next, the mold bleaching test and odor test were carried out as noted above using the obtained mold removal compositions. The results are shown in Table I.

APPLICATION EXAMPLES 5 AND 6

Mold removal compositions were prepared by changing the hydrogen peroxide aqueous solution into sodium percarbonate or sodium perborate monohydrate. The sodium hydroxide was reduced. The quantity of sodium percarbonate or sodium perborate monohydrate used was expressed in terms of the content of hydrogen peroxide. The results of the mold bleaching test and odor test carried out by using the obtained mold removal composition and pH of mold removal composition are shown in Table I.

COMPARATIVE EXAMPLE 1

A mold removal composition was prepared using sodium hypochlorite as shown in Table II. % expresses weight percent. The results of the mold bleaching test and odor test with the obtained mold removal composition and the pH of the mold removal composition are shown in Table II. The mold bleaching property was favorable, but the chlorine odor was strong.

COMPARATIVE EXAMPLE 2

A mold removal composition was prepared in the same manner as Application Example 1 except for not using dicyandiamide. The results of the mold bleaching test and odor test with the obtained mold removal composition and the pH of the mold removal composition are shown in Table II. The mold bleaching performance decreased.

COMPARATIVE EXAMPLE 3

A mold removal composition was prepared in the same manner as in Application 1 except for using tetraacetylethylenediamine instead of dicyandiamide. The results of the bleaching test and odor test with the obtained mold removal composition and the pH of the mold removal composition are shown in Table II. The mold bleaching performance decreased, and the odor of the organic acid was strong.

COMPARATIVE EXAMPLE 4

A mold removal composition was prepared in the same manner as in Application Example 1 except for using cyanamide instead of dicyandiamide. The results of the mold bleaching test and odor test with the obtained mold removal composition and the pH of the mold removal composition are shown in Table II. The mold bleaching performance decreased, and there was a peculiar and irritating odor.

COMPARATIVE EXAMPLE 5

A mold removal composition was prepared in the same manner as in Application Example I except for not using sodium hydroxide. The pH of the mold removal composition was 5.0. The result of the mold bleaching test and odor test with the obtained mold removal composition are shown in Table II. The mold bleaching performance decreased.

COMPARATIVE EXAMPLE 6

A mold removal composition was prepared in the same manner as in Application Example 1 except for having reduced the quantity of sodium hydroxide used and having made the pH of the solution 7.0. The results of the mold bleaching test and odor test with the obtained mold removal composition and the pH of the mold removal composition are shown in Table II. The hydrogen peroxide decomposed, and the mold bleaching performance decreased slightly.

COMPARATIVE EXAMPLE 7

A mold removal composition was prepared in the same manner as in Application Example 1 except for increasing the quantity of alkali agent used to make the pH of the solution 13.5. The results of the mold bleaching test and odor test with the obtained mold removal composition and the pH of the mold removal composition are shown in Table II. The hydrogen peroxide decomposed, and the mold bleaching performance decreased slightly.

As can be seen from the results of Comparative Examples 5–7, when the pH of mold removal composition is not within the range of 8.0–13.0, the mold bleaching performance decreases.

COMPARATIVE EXAMPLE 8

A mold removal composition was prepared in the same manner as Application Example 5 except for not using dicyandiamide. The results of the mold bleaching test and odor test with the obtained mold removal composition and the pH of the mold removal composition are shown in Table II. The mold bleaching performance decreased.

TABLE I

| Application Examples: | 1 | 2 | 3 | 4 | 5 | 6 |
|---|---|---|---|---|---|---|
| Composition of the Aqueous Solution | | | | | | |
| Hydrogen Peroxide | 3.0% | 5.0% | 1.5% | 20% | — | — |
| SPC* | — | — | — | — | 3.0% | — |
| PB** | — | — | — | — | — | 2.0% |
| Dicyandiamide | 3.0% | 0.5% | 2.0% | 5.0% | 3.0% | 3.0% |
| Sodium Hydroxide | 2.0% | 1.5% | 1.0% | 5.0% | 0.1% | 0.1% |
| pH | 11.4 | 10.6 | 11.3 | 9.7 | 10.4 | 10.9 |
| Test Results | | | | | | |
| Mold Bleaching Test | III | III | III | III | III | III |
| Odor Evaluation | O | O | O | O | O | O |

*SPC: Sodium percarbonate (indicated in terms of hydrogen peroxide content)
**PB: Sodium perborate monohydrate (indicated in terms of hydrogen peroxide content)

TABLE II

| Comparative Examples | 1 | 2 | 3 | 4 | 5 | 6 | 7 | 8 |
|---|---|---|---|---|---|---|---|---|
| Composition of the Aqueous Solution | | | | | | | | |
| Hydrogen Peroxide | — | 3.0% | 3.0% | 3.0 | 3.0% | 3.0% | 3.0% | 3.0% |
| SPC* | — | — | — | — | — | — | — | 3.0% |
| Dicyandiamide | — | — | — | — | 3.0% | 3.0% | 3.0% | — |
| TAED** | — | — | 3.0% | — | — | — | — | — |
| Cyanamide | — | — | — | 3.0 | — | — | — | — |
| Sodium Hydroxide | — | 2.0% | 2.0% | 2.0 | — | 0.05% | 12% | — |
| Sodium Hypochlorite | 3.0% | — | — | — | — | — | — | — |
| pH | 12.5 | 11.4 | 11.4 | 11.4 | 5.0 | 7.0 | 13.5 | 9.6 |
| Test Results | | | | | | | | |
| Mold Bleaching Test | III | I | II | I | I | I | II | I |
| Odor Evaluation | X | O | X | Δ | O | O | O | O |

*SPC: Sodium percarbonate (indicated in terms of hydrogen peroxide content)
**TAED: Tetraacetylethylenediamine

INDUSTRIAL APPLICABILITY

According to said invention, a mold removal composition of superior bleaching strength with respect to molds adhered to furnishing and walls of homes, particularly, on the kitchen sinks and bathroom walls, ceilings, and tiles and a mold bleaching method are provided.

We claim:

1. A mold removal composition, comprising:

(a) 0.2–30 wt % of dicyandiamide;

(b) 0.1–10 wt % of an alkali metal hydroxide or alkaline-earth metal hydroxide;

(c) 40–99 wt % of water; and (d) 0.5–59.7 wt % of a peroxide, wherein the pH of the composition is 8.0–13.0.

2. A method of bleaching mold from a substrate, comprising applying to the substrate a composition comprising:

(a) 0.2–30 wt % of dicyandiamide;

(b) 0.1–10 wt % of an alkali metal hydroxide or alkaline-earth metal hydroxide;

(c) 40–99 wt % of water; and (d) 0.5–59.7 wt % of a peroxide, wherein the pH of the composition is 8.0–13.0.

* * * * *